United States Patent [19]

Digenis et al.

[11] Patent Number: 6,153,756
[45] Date of Patent: Nov. 28, 2000

[54] SOLUBLE PRODRUGS OF PACLITAXEL

[76] Inventors: George A. Digenis; Kenneth H. Kortright, both of Baker Norton Pharmaceuticals, Inc., 4400 Biscayne Blvd., Miami, Fla. 33137

[21] Appl. No.: 08/868,135

[22] Filed: Jun. 3, 1997

Related U.S. Application Data

[60] Provisional application No. 60/018,926, Jun. 4, 1996.

[51] Int. Cl.$^7$ ....................... C07D 405/02; C07D 305/14
[52] U.S. Cl. ..................... 546/281.7; 549/510; 549/511
[58] Field of Search .................. 546/281.7; 514/358, 514/449; 549/510, 511

[56] References Cited

U.S. PATENT DOCUMENTS

| | | | |
|---|---|---|---|
| 5,274,137 | 12/1993 | Nicolaou et al. | 549/510 |
| 5,422,364 | 6/1995 | Nicolaou et al. | 514/449 |
| 5,440,057 | 8/1995 | Nicolaou et al. | 549/511 |
| 5,461,169 | 10/1995 | Nicolaou et al. | 549/510 |
| 5,481,007 | 1/1996 | Nicolaou et al. | 549/229 |
| 5,484,809 | 1/1996 | Hostetler et al. | 514/449 |
| 5,504,222 | 4/1996 | Nicolaou et al. | 549/511 |
| 5,608,087 | 3/1997 | Nicolaou et al. | 549/510 |
| 5,731,334 | 3/1998 | Wrasidlo | 549/510 |

FOREIGN PATENT DOCUMENTS

WO 97/15571   1/1997   WIPO.

OTHER PUBLICATIONS

Nicolaou et al., *Nature*, 364: 464–466 (1993).

Nicolaou et al., *Angew. Chim. Int. Engl.*, 33: 1583–1587 (1994).

Long et al., *Proc. Am. Assoc. Canc. Res.*, 36: 455, No. 2714 (1995).

Greenwald et al., *J. Med. Chem.*, 39: 424–431 (1996).

Nicolaou et al. (1995) *J. Am Chem. Soc.* 117(9):2409–2420.

Paloma et al. (1994) *Chemistry & Biology* 1:107–122.

*Primary Examiner*—Ba K. Trinh
*Attorney, Agent, or Firm*—Ivax Corporation

[57] ABSTRACT

Novel 2'-onium salts of paclitaxel act as prodrugs in mammalian patients to yield paclitaxel in vivo. Methods of synthesizing these onium salts are disclosed, as are methods of treating patients suffering from paclitaxel-responsive diseases by administering effective amounts of the onium salts and pharmaceutical compositions containing the novel salts which are suitable for administration to patients requiring paclitaxel therapy.

12 Claims, No Drawings

SOLUBLE PRODRUGS OF PACLITAXEL

CROSS-REFERENCE TO RELATED APPLICATIONS

This application claims the priority of provisional application Ser. No. 60/018,926, filed Jun. 4, 1996.

REFERENCE TO DISCLOSURE DOCUMENT

This application incorporates material included in Disclosure Document No. 398748, filed May 21, 1996.

BACKGROUND OF THE INVENTION

1. Field of the Invention

The invention relates to compounds which act as prodrugs for the anti-cancer agent paclitaxel and which are substantially water-soluble, as well as pharmaceutical compositions containing such prodrugs and methods of treatment using such compositions.

2. Description of the Prior Art

Paclitaxel is a natural diterpene product isolated from the Pacific yew tree (*Taxus brevifolia*). It is a member of the taxane family of terpenes. It was first isolated in 1971 by Wani et al. (*J. Am. Chem. Soc.*, 93:2325, 1971), who characterized its structure by chemical and X-ray crystallographic methods.

Paclitaxel has been approved for clinical use in the treatment of refractory ovarian cancer in the United States (Markman et al., *Yale Journal of Biology and Medicine*, 64:583,1991; McGuire et al., *Ann. Intern. Med.*, 111:273, 1989). It is effective for chemotherapy for several types of neoplasms including breast (Holmes et al., *J. Nat. Cancer Inst.*, 83:1797, 1991) and has been approved for treatment of breast cancer as well. It is a potential candidate for treatment of neoplasms in the skin (Einzig et al., *Proc. Am. Soc. Clin. Oncol.*, 20:46) and head and neck carcinomas (Forastire et al. *Sem. Oncol.*, 20:56, 1990). The compound also shows potential for the treatment of polycystic kidney disease (Woo et al., *Nature*, 368:750, 1994), lung cancer and malaria.

Paclitaxel is only slightly soluble in water and this has created significant problems in developing suitable injectable and infusion formulations useful for anticancer chemotherapy. Some formulations of paclitaxel for IV infusion have been developed utilizing CREMOPHOR EL™ (polyethoxylated castor oil) as the drug carrier because of paclitaxel's aqueous insolubility. For example, paclitaxel used in clinical testing under the aegis of the NCI has been formulated in 50% CREMOPHOR EL™ and 50% dehydrated alcohol. CREMOPHOR EL™, however, when administered intravenously, is itself toxic and produces vasodilation, labored breathing, lethargy, hypotension and death in dogs. It is also believed to be responsible for the allergic-type reactions observed during paclitaxel administration.

In an attempt to increase paclitaxel's solubility and to develop safer clinical formulations, studies have been directed to synthesizing paclitaxel analogs where the 2' and/or 7-position is derivatized with groups that would enhance water solubility. These efforts have yielded prodrug compounds that are more water-soluble than the parent compound and that display the cytotoxic properties upon activation. One important group of such prodrugs includes the 2'-onium salts of paclitaxel and docetaxel, particularly the 2'-methylpyridinium acetate (2'-MPA) salts (see Nicolaou et al., *Angew. Chim. Int. Engl.*, 33:1583–1587, 1994).

We have recently discovered that the paclitaxel onium salt 2'-MPA paclitaxel is difficult to prepare in substantially pure form and yields of the pure salt by the syntheses proposed in the scientific and patent literature are very low. This is primarily because these syntheses yield initially no more than 65–70% of the salt in mixture with paclitaxel (and small amounts of other impurities). After being separated from paclitaxel by HPLC in a solvent containing excess acetate ion (e.g., ammonium acetate), the salt decomposes rapidly, upon concentration of the HPLC effluent, to paclitaxel and very little of the 2'-MPA can be isolated. The poor yield of pure prodrug onium salt is a major inhibition to development of such a product as a commercially viable pharmaceutical because the paclitaxel starting material is extremely expensive and it is not feasible to use substantial quantities of paclitaxel to produce minute amounts of pure or substantially pure prodrug end product.

Improved prodrugs of paclitaxel which are both highly soluble in water, stable and relatively simple to prepare in high yield and purity are required.

SUMMARY OF THE INVENTION

We have prepared and tested for solubility and stability certain prodrugs of paclitaxel which are 2'-onium salts like the prior art paclitaxel 2'-MPA, but which have unexpected beneficial features not exhibited by the known paclitaxel 2'-onium salts. These include the 2'-methylpyridinium mesylate, phosphate and bicarbonate.

Injectable or oral pharmaceutical compositions may be prepared comprising aqueous solutions of the novel onium salts and, optionally, additional pharmaceutically acceptable ingredients. Said compositions may be administered to patients, e.g., by intravenous (IV) infusion, bolus injection or orally to treat paclitaxel-responsive cancers and tumors.

DETAILED DESCRIPTION OF THE INVENTION

The following is the structural formula of paclitaxel:

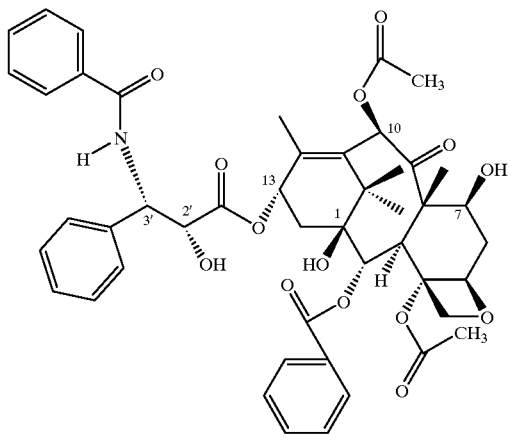

Paclitaxel

As discussed in the Background section, attempts have been made (particularly by Nicolaou et al.) to create soluble derivatives of paclitaxel, which are hydrolyzed in vivo to the active drug, by creating onium salts at the 2'-position of the parent compound. The onium salt which is indicated in the prior art as being most preferable both from the standpoint of its pharmacological activity and relative lack of toxicity (beyond the known toxicity of paclitaxel) is the 2'-methylpyridinium acetate (2'-MPA) salt of paclitaxel.

The procedures disclosed in the art for synthesizing the 2'-MPA salt yield a dry powder that is not more than 65–70% pure, the remainder of the powder consisting of paclitaxel and other minor impurities. When purification of the product is attempted by HPLC using an acetate buffer, however, the 2'-MPA that elutes from the column in the presence of an excess of acetate decomposes rapidly and only minute amounts of the pure product can be recovered. We have, therefore, conceived of and synthesized new soluble paclitaxel 2'-onium salts as soluble prodrugs for paclitaxel which, unlike 2'-MPA, can be synthesized and purified in high yields and without great difficulty. These salts have the following structural formula:

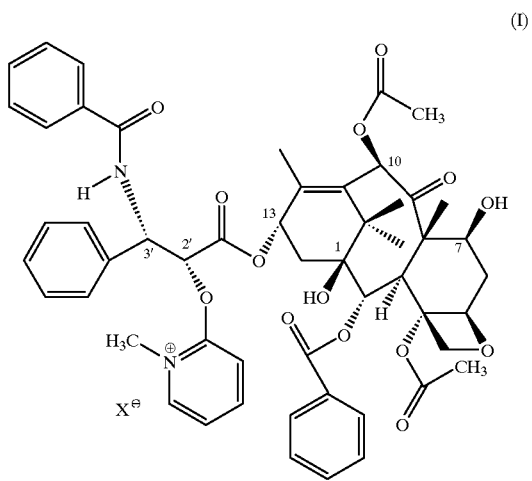

(I)

wherein $X^-$ is $CH_3SO_3^-$, $H_2PO_4^-$ or $HCO_3^-$.

Of particular interest both in terms of its physical and pharmacological properties is the compound of formula I wherein $X^-$ is the mesylate group ($CH_3SO_3^-$), i.e., the onium salt having the following structure:

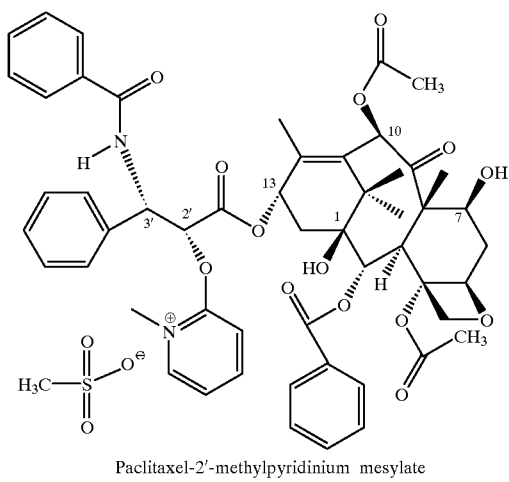

Paclitaxel-2'-methylpyridinium mesylate

The salts of Formula I may be synthesized from paclitaxel by the following general procedure:

1. Paclitaxel and 2-fluoro-1-methylpyridinium tosylate (2-FMPT) are dissolved in a substantially dry organic solvent, e.g., methylene chloride.
2. Triethylamine or another quaternary-compound forming agent is added to the foregoing mixture.
3. The mixture is stirred or agitated at room temperature and evaporated to dryness, preferably under vacuum. The dry residue is dissolved in a second organic solvent to produce a solution appropriate for high performance liquid chromatography (HPLC), for example, acetonitrile, and chromatographed by reverse phase using a mixture of the same solvent and water as the first mobile phase for an initial period, during which all fractions other than those containing the desired onium salt end product are eluted.
4. The fractions containing the desired onium salt are then eluted using a second mobile phase comprising a solution of NaX (wherein X is as defined in Formula I) in the same water/organic solvent mixture as the first mobile phase.
5. The fractions containing the onium salt are collected, concentrated and dried (for example by lyophilization) to produce an end product residue. This residue may be further purified by extraction with suitable polar organic solvents, such as methylene chloride. A non-polar solvent (e.g., hexane) is added to precipitate the product.
6. The solvents are evaporated and the residue dried to obtain the purified product.

The present invention also comprehends a method of treating a mammalian patient having a tumor, cancer, or other disease condition responsive to paclitaxel treatment by administering to said patient a pharmaceutical composition containing an effective disease treating amount of a paclitaxel onium salt prodrug according to the present invention. Paclitaxel-responsive diseases which may be treated by the invention include cancers, tumors, malignancies, uncontrolled tissue or cellular proliferation secondary to tissue injury, polycystic kidney disease and malaria. Among the cancers which may be treated are hepatocellular carcinoma, liver metastases, cancers of the gastrointestinal tract, pancreas, prostate and lung, and Kaposi's sarcoma.

The prodrugs of the invention may be administered by IV infusion, non-intravenous injection, intraperitoneally and by injection of a bolus. The prodrugs may also be administered orally to the patient in a suitable dosage form alone or together with an oral bioavailability-enhancing agent administered either (a) less than 0.5 hours before, together with or less than 0.5 hours after, (b) from about 0.5–72 hours before, or (c) both (a) and (b). Such bioavailability-enhancing agent may be selected from the group consisting of cyclosporins A through Z, (Me-Ile-4)-cyclosporin, dihydro cyclosporin A, dihydro cyclosporin C, acetyl cyclosporin A, genistein and related isoflavonoids, quercetin, calphostin, ceramides, morphine and morphine congeners. Preferred enhancing agents are cyclosporin A, cyclosporin C, cyclosporin D, cyclosporin F, dihydro cyclosporin A, dihydro cyclosporin C and acetyl cyclosporin A.

The pharmaceutical compositions containing the novel prodrugs as active ingredients may be any pharmaceutically acceptable oral, injectable or IV dosage forms. Each dosage form includes an effective amount of a prodrug (one of the novel paclitaxel-2'-onium salts) and pharmaceutically inert ingredients, e.g., conventional excipients, vehicles, fillers, binders, disintegrants, solvents, solubilizing agents, sweeteners, coloring agents and any other inactive ingredients which are regularly included in pharmaceutical dosage forms for oral administration. Suitable oral dosage forms include tablets, capsules, caplets, gelcaps, pills, liquid solutions, suspensions or elixirs, powders, lozenges, micronized particles and osmotic delivery systems. Injectable and IV dosage forms include isotonic saline solutions or dextrose solutions containing suitable buffers and preservatives. Many such dosage forms and vehicles, and listings of inactive ingredients therefor, are well-known in the art and are set forth in standard texts such as *Remington's Pharmaceutical Sciences*, 17th edition (1985).

The following are some of the advantages of using one of the novel prodrugs as the treatment drug:

1. The drug to be administered can exist as an aqueous pharmaceutical solution stored in a sterile vial, or bottled as a lyophilized powder which, when diluted with normal saline or 5% dextrose in water or other physiologically compatible solutions, can be infused intravenously into patients.

2. The drug to be administered can be stored in a liquid solution that had been frozen and upon thawing and defrosting to room temperature for several hours be given directly to the patient.

3. The drug can be stored in a DupleX™ bag (McGaw Laboratories) so that, upon breaking the seal, the powder can mix with the solvent, usually normal saline or 5% dextrose in water, and be administered directly to the patient.

4. Since the drug solution does not contain Cemophor or any solubilizing agent other than saline or dextrose solution, there is no routine need to premedicate with anti-allergy drugs (steroids, antihistamine, $H_2$ blocker).

5. The drug is expected to be given IV with an infusion time of about 1 to about 120 hours with a dose of about 100 to about 300 mg/m$^2$ per dose given about every 1 to 3 weeks. The preferred dose is about 200 mg/m$^2$ over about a 3-hour period (it is recognized that doses may need to be individualized depending on the clinical condition of the patient).

6. Because the solubility of paclitaxel-2'-MPM and the other novel salts is much higher than for paclitaxel, a smaller volume of fluid may be given with each dose than for paclitaxel, thus permitting use of this drug in patients with volume expanded related diseases such as congestive heart failure, renal disease or excessive adrenal steroid secretions.

7. The greater water solubility will permit the drug to be administered in high concentrations to the site of disease (e.g., intraperitoneal injections) or directly at a site of expected angiogenesis (post-angioplasty injury).

8. The 2'-MPM prodrug salts is orally bioavailable and may be given orally once or several times a day, if necessary with or without a bioavailability enhancer to be sure that adequate levels of paclitaxel are reached (>0.07 $\mu$M).

9. The prodrug will be useful in the adjutant treatment of various cancers (breast, bladder, ovarian, lung, bladder, esophageal and Kaposi's sarcoma) in low doses and for short infusion times (1–3 hours) since paclitaxel will be taken up by tumor cells faster because it is not protected by Cremophor which is needed to solubilize the prodrug.

10. The prodrug could be stabilized within implantable biodegradable polymers and surgically placed at or near the site of cancer where the prodrug will be released slowly and will provide the adequate local concentrations of paclitaxel.

11. Because the rate of delivery of paclitaxel from the prodrug to the hepatic microsomes may be different from paclitaxel previously exposed to Cremophor, the rate and extent of metabolite production (e.g., paclitaxel metabolites M4 and M5) may not be the same compared to paclitaxel alone.

12. Due to the polarity of the 2'-MPM salt and the generation of the mesylate component after it is given to a patient, sulfhydryl-containing conjugates will be formed which can interfere with the P 1290 kd glycoprotein or other transporter molecules. This will lead to higher intracellular levels of anticancer drugs that are subject to this pump. For this reason it is conceivable that the antitumor efficacy of 2'-MPM after IV or oral administration may be greater than that of paclitaxel, especially in multi-drug resistant tumors.

The following examples illustrate the novel onium salt prodrugs of the invention and methods of making the same. These examples are not intended, however, to limit the invention in any way or to set forth specific starting materials, reagents, reaction conditions, purification procedures or any other details which must be utilized exclusively in order to practice the present invention.

EXAMPLE 1

Paclitaxel-2'-Methylpyridinium Mesylate

In a 50 ml round bottom flask 360.2 mg (0.422 mmol) paclitaxel and 155.4 mg (0.5549 mmol, 1.31 equiv) of 2-fluoro-1-methylpyridinium tosylate (FMPT) were dissolved in 15 ml of dry methylene chloride. The reaction mixture was stirred under nitrogen atmosphere and 150 $\mu$L (1.076 mmol, 2.55 equiv) of triethylamine (TEA) was added to this reaction mixture. The colorless solution turned to a pale yellow color. The reaction mixture was stirred for 70 minutes at room temperature and then evaporated to dryness.

The residue (crude paclitaxel-2'-methylpyridinium tosylate) was dissolved in 5 ml of acetonitrile and 1.25 ml of this solution was chromatographed (total 4 injections) on a Waters 600E HPLC system using a Waters $\mu$ Bondapak steel column (19×300 mm C18, flow rate 10 ml/min). The mobile phase was 76% acetonitrile and 24% water for the first 12 minutes. Everything except the desired product was eluted and then the product was eluted using 76% acetonitrile and 24% 7.5 mmol sodium mesylate ($NaCH_3SO_3$).

All the fractions containing the product were collected and lyophilized. The residue was extracted with 200 ml of methylene chloride. The solvent was evaporated down to 50 ml and approximately 50 ml of hexane was added to precipitate the product. All the solvents were evaporated and the residue was dried on a vacuum pump for one hour to obtain the desired product, paclitaxel-2'-MPM, as a white solid, 402 mg (92%), m.p. decomposes at 119° C. Product purity by HPLC is 98%.

EXAMPLE 2

Characteristics of Paclitaxel 2'-MPM

Solubility: Deionized water (0.5 ml) was added to three samples of the 2'-MPM (1.54 mg, 0.97 mg and 0.80 mg) and the flask sonicated for approximately one (1) minute. Solution was attained in two samples (0.97 and 0.80 mgs), while the largest sample required an additional 0.1 ml to provide a free-flowing solution. The upper limit of this solubility has not been attained as yet.

Extraction: Three samples (1.2, 1.0 and 0.98 mg) were dissolved in water (1 ml) and vigorously stirred with $CH_2Cl_2$ (1 ml). The organic phase was transferred to a clean, tared vial and concentrated in vacuo. The residue was weighed and compared to the theoretical input to gauge the effectiveness of the extraction procedure. Average return for this extraction was about 44% of theoretical.

Aqueous Stability: The stability of the prodrug in $H_2O$ and 0.2M NaCl was examined at both room temperature and under refrigerated conditions. Samples in $H_2O$ (0.54 mg in 2 ml) and NaCl (0.57 mg in 2 ml) at room temperature were examined at two minute time intervals (0 through 12 minutes), 2 hours and 24 hours. Data for $H_2O$, at room temperature showed the drug to be relatively unchanged after 2 hours, with product concentration down to 56% after 24 hours. At 4° C. the product concentration was unchanged at 24 and 48 hours but decreased to 90% after 72 hours. The saline solution shows no apparent change for the first ten minutes at room temperature, 1–2% drop at 2 hours and a decrease to 70% after 24 hours. At 4° C. the product concentration was unchanged at 24 hours, was 91% at 48 hours and was 88% at 72 hours.

EXAMPLE 3

Stability of Paclitaxel 2'-Methylpyridinium Acetate

The onium salt paclitaxel-2'-MPA was prepared by the method of Nicolaou et al., *Angew. Chim. Int. Engl.,* 33:1583–1587 (1944). A 2.40 mg/ml solution of the paclitaxel-2'-MPA was prepared by dissolving the salt (10.2 mg) in a solution of water (3.024 ml) and polyethylene glycol (1.234 ml). Samples of this solution were frozen. The frozen samples were slowly warmed to room temperature and homogenized with $CH_3CN$ (50 μl). An aliquot (50 μl) was removed and diluted to a final volume of 200 μl with deionized $H_2O$ and analyzed via HPLC (20 μl injection).

Analysis conditions were as follows:

| Column: | Vydak RP C18 (#218TP54) 4.6 mm × 250 mm (5 micron) |
|---|---|
| Mobile phase: | 50% MeOH/80 mM $NH_4OAc$ |
| Flow rate: | 1.5 ml/min. |
| Wavelength | 254 nm. |
| Run time: | 45 mins. |

Results

A freshly prepared solution of the 2'-MPA derivative (0.53 mg/ml) in $CH_3CN$ provided an HPLC trace with three major peaks.

2'-MPA peak @ 28–30 mins (75%)
Paclitaxel @ 38–40 mins (15%)
Unknown peak @ 42 mins (10%)

| Stability (Room Temperature) | | | | | |
|---|---|---|---|---|---|
| | 1 Hour | 6 Hours | 18 Hours | 42 Hours | 66 Hours | 90 Hours |
| 2'-MPA % | 78% | 78% | 69 | 73% | 79% | 73% |
| Paclita. % | 14% | 14% | * | 17% | 13% | 15% |
| Unkno. % | 8% | 8% | * | 10% | 8% | 12% |

*both co-eluted, produced a large broad peak.

| Stability (4° C.) | | | | | |
|---|---|---|---|---|---|
| | 1 Hour | 6 Hours | 18 Hours | 42 Hours | 66 Hours | 2 Weeks |
| 2'-MPA % | 85% | 75% | 73% | 79% | 73% | 79% |
| Paclita. % | 15% | 11% | 10% | 9% | 11% | 9% |
| Unkno. % | * | 14% | 17% | 12% | 16% | 10% |

*No peak eluted

As set forth in Example 2, the 2'-MPM onium salt was significantly more stable than the 2'-MPA salt in aqueous solution at 4° C. (refrigerated condition). While the MPA salt had degraded to 73% after 18 hours at this temperature, the MPM salt remained unchanged at 4° C. at 24 hours and even after 72 hours had degraded only to 88–91%.

EXAMPLE 4

Paclitaxel-2'-Methylpyridinium Phosphate

The same procedure is followed as described in Example 1 with respect to the 2'-MPM salt up to the point of injection of the crude 2'-methylpyridinium tosylate into the HPLC column. 18 mg of the tosylate were injected into the column as follows:

| Column conditions: | Gradient solvent delivery starting at 50% $CH_3CN$ and 50% 5 mM $NaH_2PO_4$ to 70% $CH_3CN$ over 15 minutes. |
|---|---|
| Column: | Vydac prep. 2.2 × 25 cm (10 micron) |
| Flow rate: | 9.0 ml/min |
| Wavelength: | 254 nm |

Paclitaxel eluted after 2.55 minutes. The onium salt paclitaxel-2'-methylpyridinium phosphate ($X^- = H_2PO_4^-$ in Formula 1) eluted after 14.60 minutes.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

We claim:

1. A method of producing a 2'-onium salt of paclitaxel having the following formula:

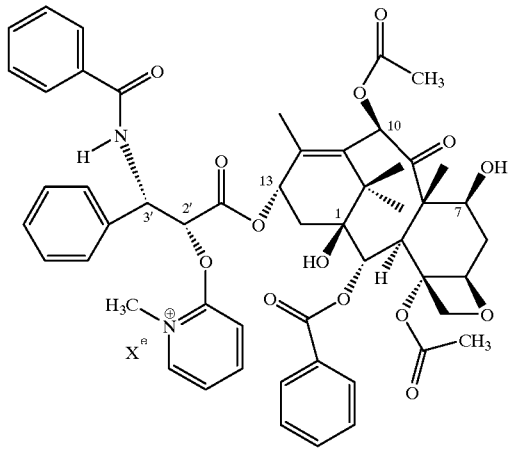

wherein $X^-$ is $CH_3SO_3^-$, $H_2PO_4^-$ or $HCO_3^-$, said method comprising:
  a) forming a mixture by dissolving paclitaxel and a 2-halo-1-onium tosylate salt in a substantially dry organic solvent;
  b) adding a quaternary compound forming agent to the mixture;
  c) stirring or agitating the mixture and evaporating it to leave a dry residue;
  d) dissolving the dry residue in a second organic solvent to produce a solution suitable for high performance liquid chromatography (HPLC);
  e) chomatographing the solution by reverse phase HPLC in an HPLC column using a mixture of said second solvent and water as a first mobile phase for an initial period during which all fractions other than those containing the desired onium salt end product are eluted from the column; and f) causing the fractions containing the desired onium salt product to elute from the column by using as a second mobile phase a solution of NaX in a mixture of said second solvent and water, wherein X is defined as above.

2. A method according to claim 1 wherein said 2-halo-onium tosylate is 2-fluoro-1-methylpyridinium tosylate.

3. A method according to claim 1 wherein said substantially dry organic solvent is methylene chloride.

4. A method according to claim 1 wherein said quaternary compound forming agent is triethylamine.

5. A method according to claim 1 wherein said second organic solvent is acetonitrile.

6. A method according to claim 1 wherein $X^-$ is $CH_3SO_3^-$.

7. A method according to claim 1 wherein $X^-$ is $H_2PO_4^-$.

8. A method according to claim 1 wherein $X^-$ is $HCO_3^-$.

9. A method according to claim 1 wherein all fractions eluting from the HPLC column which contain the desired onium salt product are collected, concentrated and dried to produce an end product residue.

10. A method according to claim 9 wherein said end product residue is further purified by extraction with a suitable polar organic solvent and the subsequent addition of a non-polar solvent to precipitate the purified onium salt end product.

11. A method according to claim 10 wherein said polar solvent is methylene chloride and said non-polar solvent is hexane.

12. A method according to claim 10 wherein said polar and non-polar solvents are evaporated after precipitation of the purified end product and said purified end product is then dried.

* * * * *